United States Patent
Kim et al.

(10) Patent No.: US 8,119,391 B2
(45) Date of Patent: Feb. 21, 2012

(54) BIOCHIP ANALYSIS SYSTEM

(75) Inventors: Soo-Kyung Kim, Seoul (KR); Seung-Yop Lee, Seoul (KR); Kyung-Ho Kim, Seoul (KR)

(73) Assignee: Nanostorage Co., Ltd., Seoul (KR)

( * ) Notice: Subject to any disclaimer, the term of this patent is extended or adjusted under 35 U.S.C. 154(b) by 651 days.

(21) Appl. No.: 10/595,425

(22) PCT Filed: Oct. 18, 2004

(86) PCT No.: PCT/KR2004/002664
§ 371 (c)(1),
(2), (4) Date: Apr. 18, 2006

(87) PCT Pub. No.: WO2005/038053
PCT Pub. Date: Apr. 28, 2005

(65) Prior Publication Data
US 2008/0192588 A1   Aug. 14, 2008

(30) Foreign Application Priority Data

Oct. 18, 2003  (KR) .......... 10-2003-0072749
Oct. 18, 2003  (KR) .......... 10-2003-0072750
May 3, 2004    (KR) .......... 10-2004-0031057

(51) Int. Cl.
*C12Q 1/68* (2006.01)
*C12M 1/34* (2006.01)
*C12M 1/36* (2006.01)
(52) U.S. Cl. ................ 435/283.1; 435/287.2; 435/288.7
(58) Field of Classification Search .......... None
See application file for complete search history.

(56) References Cited

U.S. PATENT DOCUMENTS
5,057,685 A  10/1991  Kurosawa et al.
(Continued)

FOREIGN PATENT DOCUMENTS
JP   11-094747   4/1999
(Continued)

OTHER PUBLICATIONS
International Search Report dated Feb. 17, 2005 from PCT/KR2004/002664.

*Primary Examiner* — Betty Forman
(74) *Attorney, Agent, or Firm* — Fox Rothschild LLP

(57) ABSTRACT

The present invention relates to a biochip readout device for analyzing and reading out biochips in a rotation manner such that a biochip having been adopted in a non-rotation manner is mounted on an optical disc, and a diagnostic system with a biochip readout device. The biochip readout device comprises biochip cartridge shaped as a rotatable disc, wherein a biochip is installed on or within the disc, a disc rotation drive unit being driven such that the biochip cartridge is rotated, a light reception means for receiving a beam reflected from the disc, the light reception means having a light source scanning the disc with the beam, a focusing/tracking controlling unit for controlling a focusing and tracking operation using the beam received by the light reception means, an optical pick-up unit having an objective lens drive unit for tracking a focus and track of the light source, an optical pick-up device having a bio analysis signal generation unit for receiving a light excited by the biochip and outputting a bio analysis signal and a system and output controlling unit for outputting monitoring bio analysis information, the system and output controlling unit having a signal processing unit for processing and analyzing the bio-analysis signal corresponding to bio analysis information to generate the monitoring bio analysis information.

5 Claims, 16 Drawing Sheets

U.S. PATENT DOCUMENTS

| | | | |
|---|---|---|---|
| 5,922,617 A * | 7/1999 | Wang et al. | 436/518 |
| 6,545,758 B1 * | 4/2003 | Sandstrom | 356/317 |
| 7,141,416 B2 * | 11/2006 | Krutzik | 435/288.5 |
| 7,709,248 B2 * | 5/2010 | Yamatsu et al. | 435/287.2 |
| 2005/0048595 A1 * | 3/2005 | Yamatsu et al. | 435/18 |

FOREIGN PATENT DOCUMENTS

| | | |
|---|---|---|
| KR | 2001-39264 A | 5/2001 |

* cited by examiner

BIOCHIP ANALYSIS SYSTEM

TECHNICAL FIELD

The present invention relates to a biochip readout device for analyzing and reading out biochips in a rotation manner such that a rectangular shaped biochip having been adopted in a non-rotation manner is installed on an optical disc, and a diagnostic system with the biochip readout device.

More particularly, the present invention relates to a biochip readout device for being implemented based on a structure of a general optical disc reproduction device, detecting a biochip based on readout of fluorescence intensity of fluorescent dye combined with a labeling sample solution, and detecting and analyzing bio-information combined with the biochip based on the fluorescence intensity, and a diagnostic system with the biochip readout device.

Especially, the present invention is related to a biochip readout device for detecting and analyzing bio-information combined with a bio-chip to record the analysis result of the biochip in a predetermined area of an optical disc on which bio-chips are mounted, reading out the analysis result of the biochip recorded in the optical disc using a general optical disc reproduction device to output the readout result on a display connected to the optical disc reproduction device, and a diagnostic system with the biochip readout device.

Also, the present invention relates to a biochip readout device designed to be adopted to biochips with various sized cells, and a diagnostic system with the biochip readout device.

BACKGROUND ART

In general, a biochip is a biological microchip manufactured as bio-molecules such as DNA, proteins etc. are combined with blood or urine of a tester on a relatively small substrate so that generic defects, protein distributions, reaction aspects etc. can be analyzed. Biochips have attracted attention in fields such as pharmaceutical development, environment monitoring, etc. as well as clinical diagnosis such that marketability is highly evaluated in the future. In order that such a biochip is utilized for a sensor for diagnosis and monitoring of environments/foods etc., it is preferably implemented with a type of biosensor capable of being easily portable and directly analyzing samples at the work field. Therefore, it is necessary to develop biochips such that they have a relatively high processing speed and low manufacturing costs. Also, it is very important to form First-to-market in the biochip fields. Because biochips are used not only in the laboratory but also in information construction for a database, if a product introduced before generally selling on a market constructs a database and gets to be a standard based on the constructed database, it is difficult to replace the product having been a standard with another product in that market. Therefore, based on the aspect, certain companies having previously occupied the biochip fields have great advantages. The biochip markets are formed in the mid-1990s and rapidly raised around in the center of some product- and service-oriented companies in these days, but it is still an initial stage considering the entire technology. Therefore, this field needs to be continuously researched through novel ideas.

In one analysis method using biochips, blood or urine etc. of a testee is reacted with a biochip integrated with protein and florescent dye responding to a particular disease or symptom. After that the method diagnoses whether the testee has the particular disease or symptom as fluorescent dye revealed by activated between the proteins of the biochip and the proteins included in the blood or urine are analyzed. The biochip for diagnosing a particular disease or symptom is called as a diagnosis kit. The diagnosis kits may be categorized based on promptness and precision. Generally, biochips are analyzed by naked eye or under a microscope. However, the bio-chip test by naked eye requires a relatively high skillful experience of the examiners because it is dependent on only his/her determination. Therefore, reliability of the bio-chip analysis results may be decreased due to examiner error. Also, precision of the analysis results may be decreased by internal or external factors such as examiner fatigue, analysis environments, etc. Meanwhile, even though the microscopic test has a higher reliability than the test by naked-eye of the examiner, it requests much examining time and examiners.

Generally, biochip manufacturing methods are classified into micro-array and micro-fluidics.

① Micro-array:

It is typically used for a DNA chip, a protein chip, etc., in which they are constructed as thousands or tens of thousands of DNAs or proteins etc. are evenly aligned and spaced from each other to attached on a substrate such that coupling aspects thereof can be analyzed based on a processing operation of targeted analysis materials. The protein chip has more valuable than the relatively well-known DNA chip considering that most biological phenomena occurs at the protein level. But, unlike DNA, the protein chip has less developed and commercialized than the DNA chip due to difficulty in securing corresponding proteins such as enzymes, antibodies, receptors, etc. and the easily changeable and denaturable nature of proteins.

② Micro-fluidics Manner:

The micro-fluidics manner is also called 'Lab-on-a-Chip'. It is used for biochips capable of analyzing aspects reacting with various bio molecules or sensors, which are integrated with a chip while a small quantity of targeted analysis materials are flowing. Recently, chips capable of performing separation of analysis material, synthesis, quantitative analysis etc. have been researched.

Biochips manufactured by the above-mentioned manners are aligned according to desired location information, respectively, and detected by a method for labeling florescent dye. The sample solution labeled by the fluorescent dye and the bio-information fixed to the substrate are reacted to each other under general coupling reaction conditions so as to monitor the degree of selective coupling.

Such biochips are typically detected by laser induced fluorescing detection. Laser induced fluorescing detection is performed like that fluorescent dye is excited as the florescent dye absorbs light emitted from a light source, in which the light source emits the laser beam at a wavelength capable of being absorbed by the fluorescent dye, and then the amount of fluorescence emitted when the fluorescent dye changes from the excited state to the ground state is measured, thereby determining density thereof from each of the fluorescence intensities. Based on the method, a DNA sample can be quantitatively analyzed when fluorescent dye is added thereto. One of the most commonly used apparatuses for detecting fluorescence using the laser induced fluorescing detection method is a confocal laser scanning system. The confocal laser scanning system employs a laser as a light source and inputs fluorescent signals emitted from a sample through a specific detector such as a photomultiplier tube or an avalanche photo diode to convert the fluorescent signals into a digital image. Namely, fluorescence emission is induced as only light emitted from a laser source is scanned to a sample labeled by fluorescent dye, in which the wavelength band of the light emitted from the laser source is proper to excite the fluorescent dye. Here, various filters such as a beam splitter etc. can be used. At the last stage, a pinhole as a filter can be located in front of a detector such that only a confocal image is received. As such, the confocal laser scanning system requires a preferable selection etc. and has an advantage in that out of focus images can be eliminated. At the present stage of development, it is important to advance sensitivity of a fluorescence detection device in a laser induced fluorescing detection apparatus and a technology therefor. One of the major factors to advance the sensitivity of the fluorescence detection device is to collect maximum fluorescence radiation and to minimize background radiation. Therefore, in order to obtain an optimal detection limit in the laser induced fluorescing detection apparatus, fluorescence emitted from a test sample labeled by fluorescent dye should be collected with a high efficiency and distribution of excited light reaching the fluorescence detection device can be minimized. Substantially, an objective lens having a relatively high aperture or a mirror is used for fluorescence collection. Light collection by a lens is related to aperture of the lens and refraction index of peripheral media. Such a relationship can be expressed by the following equation (1).

$$\text{Collection efficiency} = \frac{1}{2}\left(1 - \cos(\sin^{-1}(NA))\right) = \frac{1}{2}\left(1 - \cos\left(\sin^{-1}\left(\frac{1}{2F}\right)\right)\right) \quad (1)$$

Where F denotes numerical aperture (F-number) and NA denotes effective numerical aperture.

Generally, a light collection lens is surrounded by air, which has a refractive modulus of 1. From the above equation (1), it can be easily appreciated that a lens having a relatively large numerical aperture is required to obtain high collection efficiency. For example, if a lens has a numerical aperture of 1, it can collect 50% of light emitted from the test sample. Also, according to the collection efficiency equation, a lens surrounded by air with a numerical aperture of 0.5 can collect only 7% of emitted light.

In the prior art refractive or reflective optical collectors having optical fibers are used for collecting emitted fluorescence radiation. However, fluorescent light collection efficiency of these collectors is limited by their maximum collection angle. As shown in FIG. 25, a typical highly efficient collector has a collection cone angle of about 90°, which corresponds to a collection efficiency of 14% in the laser induced fluorescing detection apparatus.

Even though such a confocal laser scanning system has a high sensitivity and precision, it is expensive and occupies a large volume for installation.

Especially, in the confocal laser scanning system, since a chip for requiring an accuracy of less than 1 μm or monitoring large amounts of information is proper to used therefor, a biochip is difficult to be generally adopted therein.

Also, since the confocal laser scanning system scans fluorescent images and then displays images corresponding to the fluorescent images, it has disadvantages in that it requires much processing time such as scanning time and analysis time.

Also, chips manufactured by the prior art methods are evenly aligned row by row and patterned in a land/groove manner using XY linear stages. However, in order to construct disc-type biochips, the prior art methods must be designed for patterning the biochips along the periphery of the disc thereon.

DISCLOSURE

Technical Problem

Therefore, the present invention has been made in view of the above problems, and it is an object of the present invention to provide a biochip readout device for analyzing and reading out biochips in a rotation manner such that a rectangular shaped biochip having been adopted in a non-rotation manner is installed on an optical disc, and a diagnostic system with the biochip readout device.

It is another object of the present invention to provide a biochip readout device implemented based on a structure of a general optical disc reproduction device, detecting a biochip based on readout of fluorescence intensity of fluorescent dye combined with a labeling sample solution, and detecting and analyzing bio-information combined with the biochip based on fluorescence intensity, and a diagnostic system with the biochip readout device.

It is further another object of the present invention to provide a biochip readout device for detecting and analyzing bio-information combined with a bio-chip to record the analysis result of the biochip in a predetermined area of an optical disc on which bio-chips are mounted, reading out the analysis result of the biochip recorded in the optical disc using a general optical disc reproduction device to output the readout result on a display connected to the optical disc reproduction device, and a diagnostic system with the biochip readout device.

It is another object of the present invention to provide designed to be adopted to biochips with various sized cells, and a diagnostic system with the biochip readout device.

It is an object of the present invention to provide a biochip readout device capable of being compatible, implemented in a small size and low manufactured in low costs as compared with a scanner manner adopted in conventional biochips, as it is implemented to have a structure identical to the conventional optical reproduction device, and a diagnostic system with the biochip readout device.

It is an object of the present invention to provide a biochip readout device capable of detecting relatively clear images as biochips are spotted to form a pattern evenly spaced on an optical disc by a land/groove manner comparing with the conventional manner, of having a relatively fast patterning speed due to taking a rotation manner and of having a relatively fast detection speed since biochips are formed in a disc type, and a diagnostic system with the biochip readout device.

It is an object of the present invention to provide a biochip readout device capable of reading out fluorescent intensity of fluorescent dye combined with a sample solution labeled by optical system of the conventional optical storage device in twice times than fluorescent intensity of the conventional biochips using a selective wavelength reflection film and detecting biochips based on the reading out, and detecting and analyzing combined with biochips, and a diagnostic system with the biochip readout device.

It is an object of the present invention to provide a biochip readout device capable of rapidly processing and analyzing disc-type biochips as various biochips can be separatably installed on the upper surface of the type of disc and of overcoming limitation of the conventional biochip, wherein a biochip scanner cannot be compatible with other biochips using a conventional device, and a diagnostic system with the biochip readout device.

It is an object of the present invention to provide a biochip readout device capable of performing highly accurate detection since light spot size of an optical disc recording/reproducing device is less than 1 μm, and of being designed such that biochips having various cell sizes can be adopted thereto, and a diagnostic system with the biochip readout device.

Technical Solution

In accordance with an aspect of the present invention, the above and other objects can be accomplished by the provision of a biochip readout device comprising: biochip cartridge shaped as a rotatable disc, wherein a biochip is installed on or within the disc; a disc rotation drive unit being driven such that the biochip cartridge is rotated; a light reception means for receiving a beam reflected from the disc, the light reception means having a light source scanning the disc with the beam; a focusing/tracking controlling unit for controlling a focusing and tracking operation using the beam received by the light reception means; an optical pick-up unit having an objective lens drive unit for tracking a focus and track of the light source; an optical pick-up device having a bio analysis signal generation unit for receiving a light excited by the biochip and outputting a bio analysis signal; and a system and output controlling unit for outputting monitoring bio analysis information, the system and output controlling unit having a signal processing unit for processing and analyzing the bioanalysis signal corresponding to bio analysis information to generate the monitoring bio analysis information.

In accordance with another aspect of the present invention, there is provided a diagnostic system having a biochip readout apparatus, comprising: a biochip readout device including: biochip cartridge shaped as a rotatable disc, wherein a biochip is installed on or within the disc; a disc rotation drive unit driven such that the biochip cartridge is rotated; a light reception means for receiving a beam reflected from the disc, the light reception means having a light source scanning the disc with the beam; a focusing/tracking controlling unit for controlling a focusing and tracking operation using the beam received by the light reception means; an optical pick-up unit having an objective lens drive unit for tracking a focus and track of the light source; an optical pick-up device having a bio analysis signal generation unit for receiving a light excited by the biochip and outputting a bio analysis signal; and a system and output controlling unit for outputting monitoring bio analysis information, the system and output controlling unit having a signal processing unit for processing and analyzing the bio analysis signal corresponding to bio analysis information to generate the monitoring bio analysis information; and a diagnosis device for comparing the monitoring bio information for monitoring image signal from the biochip readout device with reference data and proving an analysis result generated based on a result of the comparing operation to a user, wherein the reference data for monitoring bio-information of the biochip are constructed in database format in the diagnosis device.

Advantageous Effects

As described above, the biochip readout system according to the present invention is implemented based on a general CD/DVD device. Also, the biochip readout device employs a beam whose spot size is under 1 μm, rotates a circular recordable disc at a relatively high speed of 7200 rpm, and accurately reads/records a relatively large amount of information at a high transmission rate (1.38 Mb/s) from/in the recordable disc. Therefore, the present invention can advance analysis speed than the conventional fluorescent confocal scanner.

Also, the present invention has advantages in that its manufacturing costs and size can be reduced, and its analysis speed and precision can be improved, compared with the conventional biochip readout device. Also, the present invention does not require an additional device such as an analysis device.

Also, since the present invention does not requires an additional device according to cell size (beam spot size) and can read information based on disc type, it can be provided to consumers in various fields such as medicine, environmental science, chemistry, biology, process, foods and information communication fields. Especially, a core technology of the present invention for biochip detection can be provided to major companies in the relevant to the present invention, thereby creating a high added value therefrom.

Also, the cartridge for biochip installation and the disc type biochip according to the present invention can be adopted to a microarray structure without changing the structure of the biochips, in which the micro array structure is patterned as a rectangle, which is known as it is difficult to detect by a disc.

Also, the present invention can be commonly used for various biochips, while the conventional biochips must be manufactured depending on its capacity and usage, respectively, and thusly requires additional devices necessary for corresponding to each biochip.

Also, the disc type biochip adopting the present invention can be simply implemented such that it needs relatively low manufacturing costs. Also, since the disc type biochip agitates the sample solution, binding rate is high and analysis time can be reduced.

Also, since the present invention can extend the conventional limited diagnosis market such as a research institute and hospitals etc. to a self-diagnosis market, the present invention can be used in a relatively wide field.

In the cell patterning device according to the present invention, bio-cells can be precisely located on the upper surface of the optical disc to form a bio cell pattern.

Also, since the pin module is aligned on the optical disc in the radial direction, the biochip patterns can be formed thereon according to one turn of a half turn thereof. From the alignment, the biochips can be mass-produced manufactured at a relatively high speed and at low manufacturing costs.

The present invention spots bio-cells on the optical disc forming a predetermined pattern grid with a predetermined interval in periphery directions and detects images more clearly than the conventional manner. Also, the present invention adopts a rotation manner, it has a relatively fast patterning speed. Since a disc type biochip is provided, a detecting speed can be rapidly achieved.

The present invention employs a substrate made of plastic such as polycarbonate, which is used for a CD/DVD, for highly accurate detection, while the conventional manner uses a substrate made of glass having a good flatness. Therefore, the substrate of the present invention can be easily machined to form a desired shape such as a disc type patterned biochip, which imparts the biochip with a good performance and reduces manufacturing costs reduce.

The present invention can detect biochips using conventional CD/DVD optics with the biochips fast rotated, thereby manufacturing a low-priced biochip scanner. Meanwhile, the conventional scanner is driven to detect biochips at a constant speed using a linear stage.

DESCRIPTION OF DRAWINGS

The above and other objects, features and other advantages of the present invention will be more clearly understood from the following detailed description taken in conjunction with the accompanying drawings, in which.

BEST MODE

First, the terms used in the description of the present invention are defined as below. A light fluorescent wavelength head as an element detecting second light from a light source for a DVD includes a photomultiplier tube or an avalanche photodiode. A selection wavelength reflection film reflects light of only a particular wavelength and passes therethrough for other wavelengths. The selection wavelength reflection film reflects first light for controlling focusing/tracking operation or recording/reproducing operation.

Biochip Reading Out Device

Figure 1:
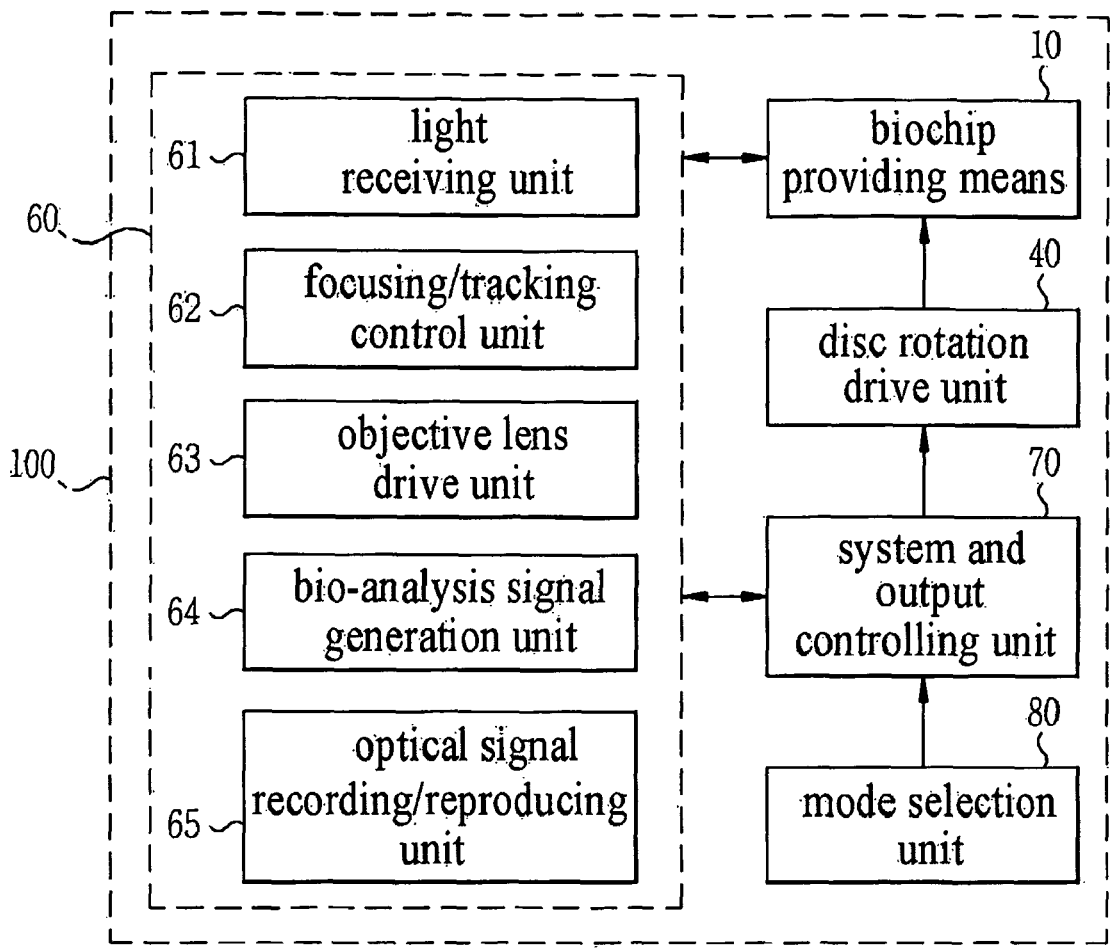
FIG. 1 is a view illustrating the construction of a biochip readout device according to the present invention.

As shown in FIG. 1, the biochip readout device 100 according to the present invention includes biochip cartridge 10 shaped as a rotatable disc on or in which biochips are mounted, a disc rotation driving unit 40 adapted to drive rotation of the biochip cartridge 10, an optical pick-up device 60, a system and output controlling unit 70 for analyzing signals of the optical pick-up device 60 to generate bio analysis information for monitoring and outputting it, in which the system and output controlling unit 70 includes a signal processing unit for processing the signals generated by the optical pick-up device 60, and a mode selecting unit 80 for selecting one of biochip readout mode and general optical recording/reproducing mode.

The optical pick-up device 60 includes a light receiving unit 61 for receiving a reflected light beam reflected from the disc, in which the light receiving unit 61 includes a light source for scanning the disc with a scanning light beam, a focusing/tracking controlling unit 62 for controlling focusing and tracking of the optical pick-up device 61 using the reflection light beam from the light receiving unit 61, an objective lens driving unit 63 for enabling the light beam of the light source to performing focusing and tracking operations on the disc, a bio-analysis signal generation unit 64 for receiving signals corresponding to light excited by the biochip and outputting bio-analysis signals and an optical recording/reproducing unit 65 for recording recording bio analysis signals at a predetermined area of the optical disc 10 in response to a control signal of the system and output controlling unit 70 and for reproducing recorded bio-analysis information.

Operations of the system and output controlling unit 70 is described in as follows. According to a user operation, the system and output controlling unit 70 outputs control signals to the disc rotation driving unit 40 such that the optical disc 10 rotates and to the optical pick-up device 60 such that the focusing and tracking operations of the optical pick-up device 60 can be controlled. Also, the system and output controlling unit 70 controls the optical pick-up device 60 for scanning the disc with second light. Also the system and output controlling unit 70 reads sample information based on signals for bio-analysis inputted from the optical pick-up device 60, converts the read sample information into a predetermined matrix structure to generate and output monitoring bio-analysis information.

The system and output controlling unit 70 forms a matrix structure such that a cell revealing florescent dye is recognized as a letter of A and other cells are recognized as a letter of ~A, and generates monitoring bio analysis information based on the matrix structure.

Figure 3:
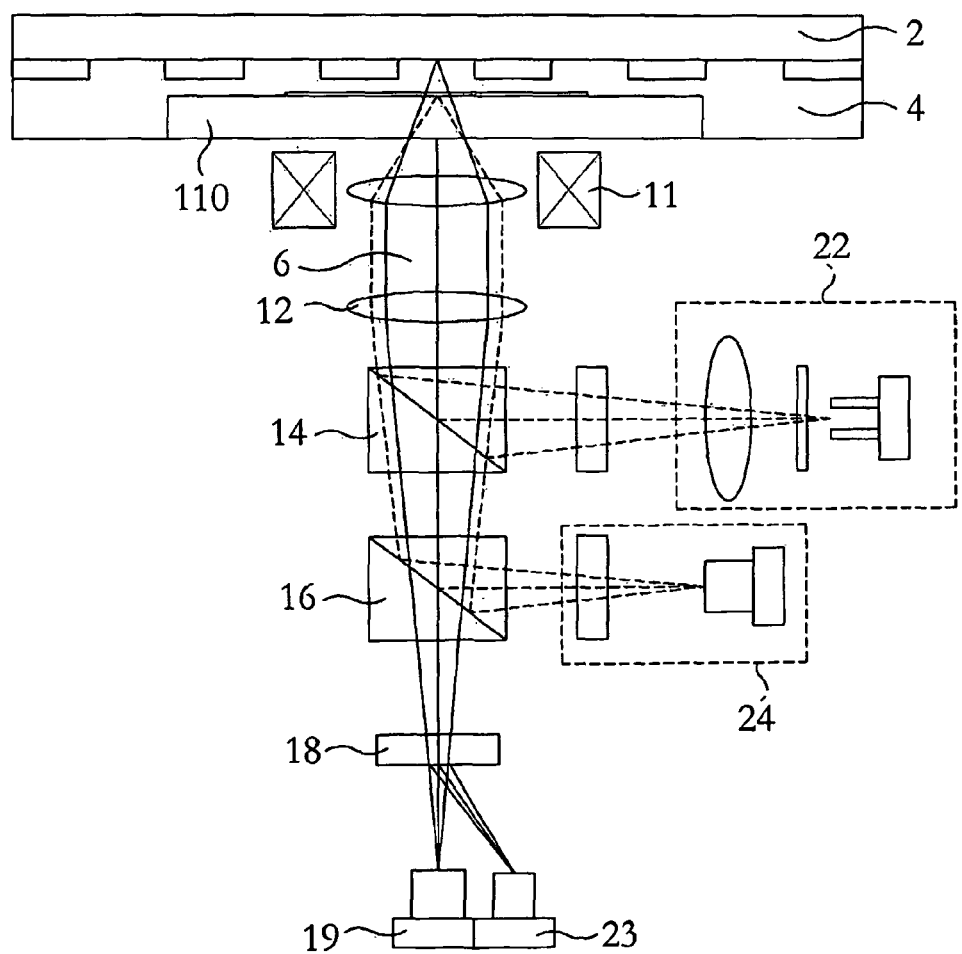

As shown in FIG. 3, the optical recording/reproducing unit 65 includes a filter 16 for receiving light for optical record/reproduction, and a head 24 having a laser diode. The bio-analysis signal generation unit 64 includes a light emitting fluorescent filter 14 for filtering a light emitting fluorescent wavelength of the lights excited by the biochip, and a light emitting fluorescent wavelength detection head 22 for detecting the filtered light emitting fluorescent wavelength in response to the control signal inputted by the system and output controlling unit 70 and for outputting the bio-analysis signal. Here, the light emitting florescent wavelength head 22 includes a PMT or APD.

Also, the optical pick-up device 60 includes a first light source 19, which emits light as shown in FIG. 3, and a second light source 23. It further includes a lens 12, etc. These elements are the same as the optical pick-up device for a CD/DVD player, thereby omitting a detailed description for those below.

The biochip readout device constructed above is operated as follows.

Firstly, when an optical disc 10 mounting bio-chips thereon is put on a disc rotation driving unit 40 and a bio-chip readout mode is selected through a mode selection unit 80, the system and output controlling system 70 controls the disc rotation driving unit 40 to be rotated and the optical pick-up device 60 such that the first and second lights can be scanned on the lower surface of the optical disc 10.

Here, the first light is incident on the focusing/tracking controlling unit 23 such that the system and output controlling unit 70 can control the actuator 14 to perform focusing/tracking operations.

The light emitting fluorescent wavelength detection head 22 of the bio-analysis signal generation unit 64 receives the filtered wavelength through the light emitting fluorescent wavelength filter 14 and converts it to a bio-analysis signal to be outputted to the system and output controlling unit 70.

Namely, the light emitting florescent wavelength detection head 22 of the optical pick-up device 60 recognizes "0" and "1" based on a reflection difference of 20%~40%.

Figure 4:
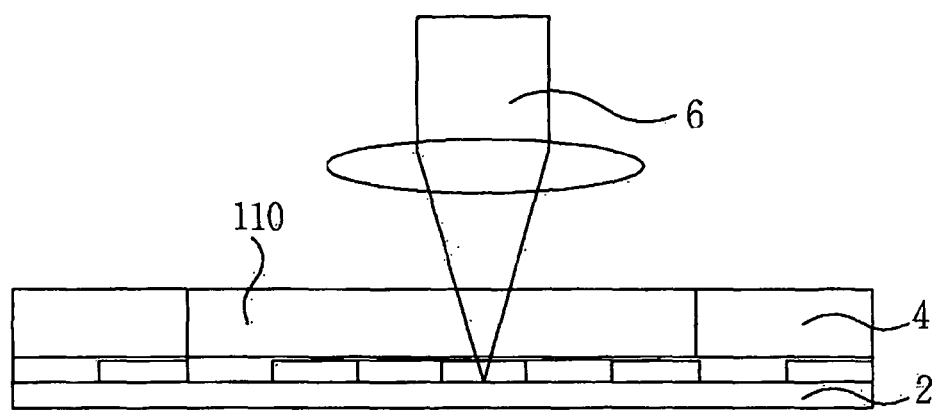
FIG. 4 is a view illustrating the structure of a single optical pick-up device.
Figure 5:
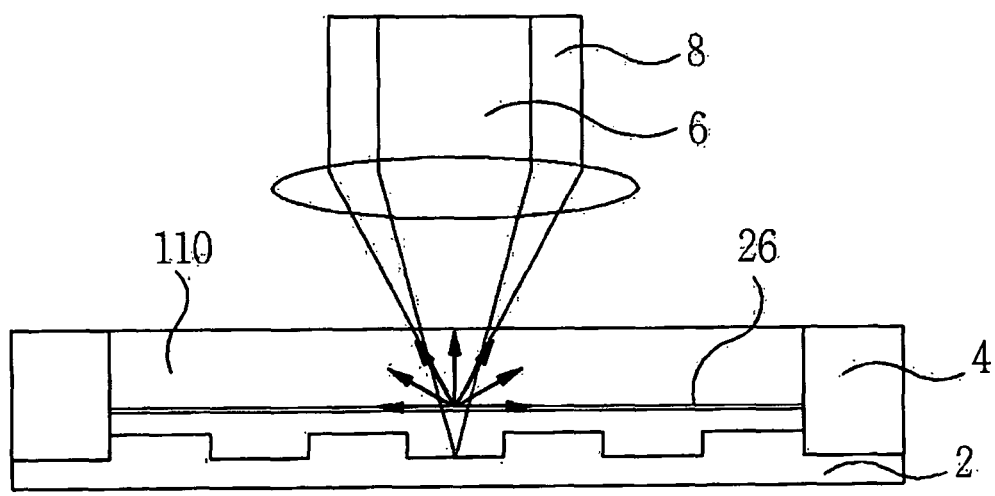
FIG. 5 is a view describing a procedure for selectively selecting only a beam scanned through a second light source of a dual optical pick-up device when a selection wavelength reflection film is attached to a biochip substrate.

As shown in FIGS. 4 and 5, an optical disc including a first substrate 2 and second substrate 4 has the same structure as a general CD/DVD. Information contained in such an optical disc is recognized by reflection difference. A biochip on the second substrate 4 emits florescence by second light 8. Fluorescent intensity of the biochip is detected and converted to a bio-analysis signal through the light emitting florescent detection head 22.

The bio-analysis signal is corrected by a correction circuit (not shown) and outputted to the system and output controlling unit 70. The system and output controlling unit 70 outputs bio-analysis information or a bio-analysis signal to be recorded in an optical disc to a monitor or the optical disc 10 with biochips mounted thereon.

Meanwhile, when an optical recording/reproducing mode is selected through the mode selection unit 80, the recoding bio-analysis signal is recorded at a predetermined area except for the area mounting biochips in the optical disc 10 through the optical recording/reproduction unit 24.

Accordingly, a user can carry the optical disc 10 containing bio-analysis information such as DNA information and provide it to corresponding organization.

Because bio-analysis information recorded in the optical disc 10 can be reproduced by a general optical disc reproduction device installed in a computer, a user should not be examined by an additional test for generating bio-analysis information.

For example, when bio information on an individual is detected through a biochip in a hospital to record in a disc, the person can bring the disc anywhere and reproduce his/her own bio-information therein through a CD/DVD reproduction device.

Figure 2:
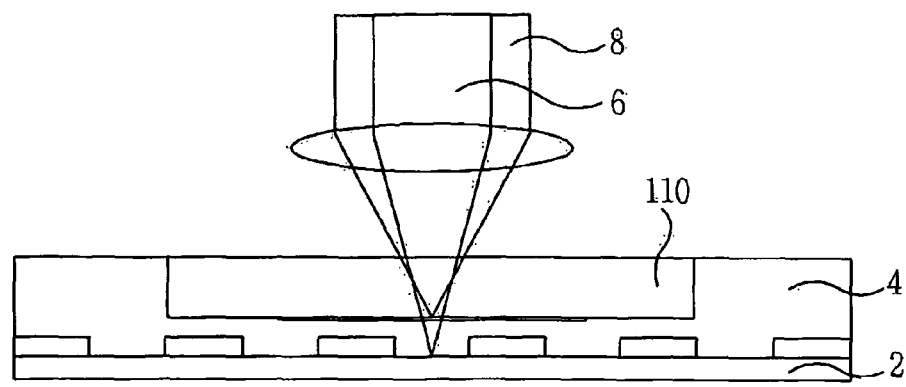
FIG. 2 and FIG. 3 are views illustrating the structure of a dual optical pick-up device.

The optical pick-up device 60 according to the present invention is implemented with a type of dual optical pick-up device, which is described in detail as below as shown in FIGS. 2 and 3. The optical pick-up device 60 uses two light sources having different laser wavelengths, in which light from a first light source 6 is used for controlling tracking and focusing operations and light from a second light source 8 is used for focusing light on a biochip and detect it there from as a biochip scanner.

Lights from the first light source 6 and the second light source 8 are tracking along the lands/grooves of the optical disc with a predetermined distance there between as the integrated optical pick-up device is operated. Here, the optical disc including a first substrate 2 and second substrate 4 is formed to have a predetermined interval there between such that the dual optical pick-up device operates properly within the predetermined interval. Here, the first substrate 2 has a structure of lands/grooves for being tracked by the dual optical pick-up device and the second substrate 4 has a structure to be inserted the biochips 110. The biochips 110 installed on the second substrate 4 are detected in a rotation manner rather than in a linear manner.

The fluorescent signal caused by the above light source can be detected by the manner shown in FIG. 3. Namely, light from the first light source 6 is reflected by a reflection film (not shown) of the first substrate 2 and the reflected light of the first light source 6 is detected by a photo-detector (PD) 23 located an optical path thereof to obtain tracking and focusing signals. The fluorescent signal detected in the biochip 110 installed in the second substrate 8 is separated from the detection wavelength by a selective filter composed of a prism 14. The light emitting fluorescent wavelength detection head 22 inputs the separated detection wavelength and detects a signal there from.

For example, if the first light source 6 is used as a CD light source and the second light source 8 is employed as a DVD light source, the CD is designed to have the following structure. Since the thickness of a CD is 1.2 mm, working distances of a CD and a DVD should be 1.32 mm and 1.5 mm, respectively. Since the thickness of a standard biochip is 1 mm, if the first substrate 2 and second substrate 4 are designed such that an interval there between is 0.18 mm, the CD can be designed to have the first substrate 2 having lands/grooves applied by the laser output having two different wavelengths and the second substrate 4 activated by a DVD laser beam.

As shown in FIG. 5, if fluorescent dye is used as Cy5 in a biochip scanner, since the excitation wavelength of the dye is 650 nm and the emission wavelength of the dye is 670 nm, a selective wavelength reflection film 26 between the biochip 110 and the disc substrate 2 is coated such that light at the scanning wavelength can pass therethrough and light at the emission wavelength can be reflected therefrom to increase collection efficiency of light more than two times of the prior art collection efficiency. For example, if the NA is 0.8, a light collection efficiency of about 40% is predicted. Therefore, since only a coating process of a selective wavelength reflection film 26 is added when manufacturing a disc, this method is of great utility. Also, the method is cost-effective in terms of manufacturing costs since only costs increase by a selective wavelength reflection film 26. In addition, even though the method is implemented in low costs, it has a relatively high performance. Since the above factors are reflected, light collection efficiency is increased as the selective wavelength reflection film 26 is coated on the substrate of the bio-chip 110.

With reference to FIG. 4, operations of a single pick-up device are described in detail below. Biochips 110 are mounted on the upper of the first substrate 2 having lands/grooves. A laser beam from a laser source 6 is used for tracking and focusing operations as well as for detection of biochips while focused on the biochip as a biochip scanner. Therefore, a single source can be used for focusing and tracking operations and biochip detection. Here, when the biochips 110 are located on the upper side of the first substrate 2, the biochips 110 should be installed such that they can be within a center of the focus of beam. For this, a structure for installing biochips in the optical disc and a manner for directly spotting the biochips on the substrate should be considered.

Biochip

Figure 6:
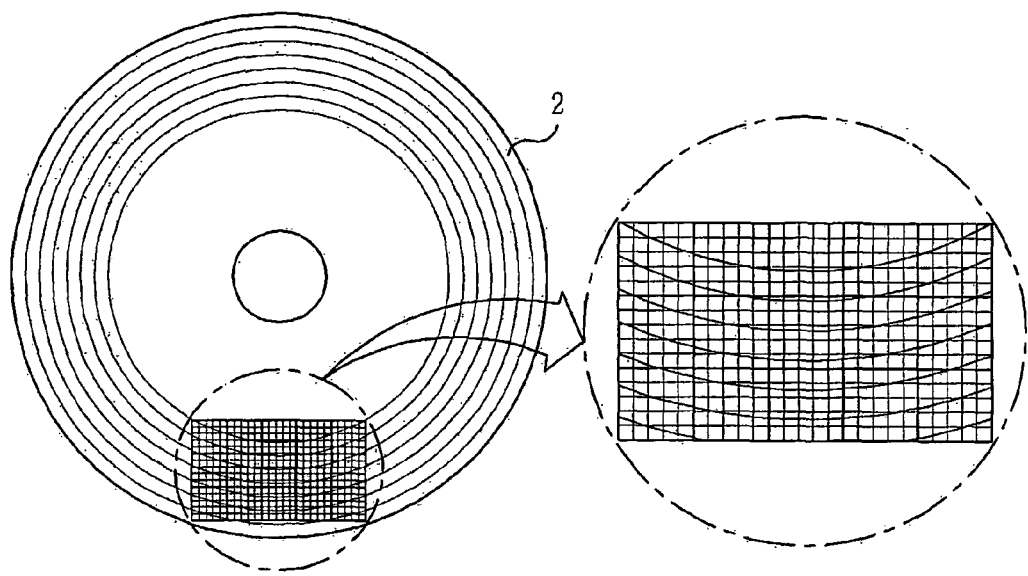
FIG. 6 is a view of a disc employing biochips according to the present invention.

With reference to FIG. 6, a biochip 110 shaped as a rectangle may be included on the upper surface of a disc 115.

Figure 7:
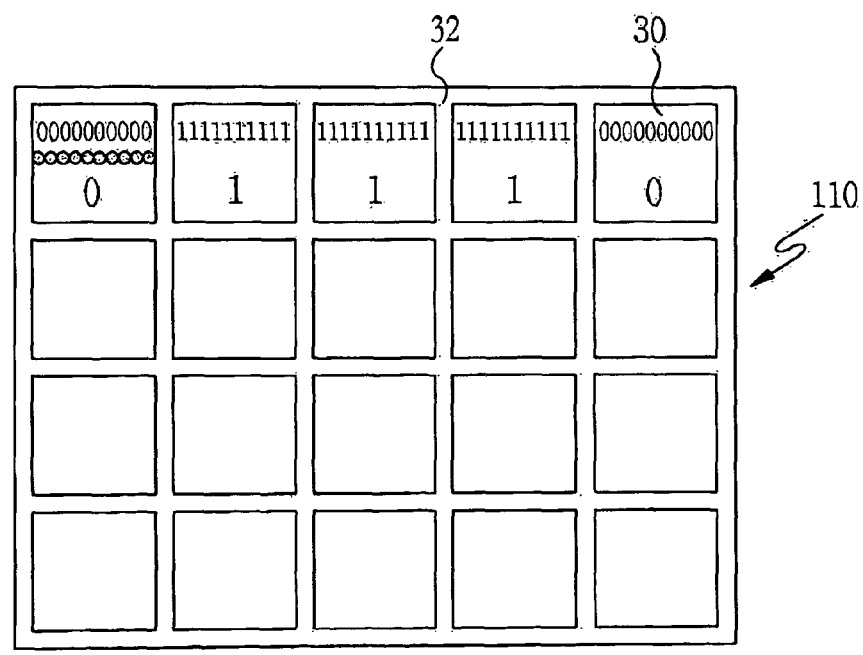
FIG. 7 is a view for describing biochips.

More specifically, as shown in FIG. 7, the biochip 110 is formed to include a plurality of cells 30 aligned in a predetermined format, in which tracks 32 are formed between the cells 30.

Because the size of the cells 30 of the biochip 110 is larger than that of a beam spot, one cell can be repeatedly detected by the laser beam. The repeatedly detected information is statistically analyzed to determine information contained in the cell. Therefore, the cell information has a relatively high precision. After that, the cell information is converted to signals patterned based on a matrix structure and then outputted thereto.

Namely, when a disc 2 is rapidly rotated, a sample is read out as the optical pick-up device, which will be described later, rapidly scans the cells using a beam. After that, the read sample information is converted into a predetermined matrix structure by a controlling unit which will be described later. The system and output controlling unit 70 controls the entire system such that bio analysis information from the matrix structure is generated and outputted to a monitor, etc.

Optical Disc

Figure 8:
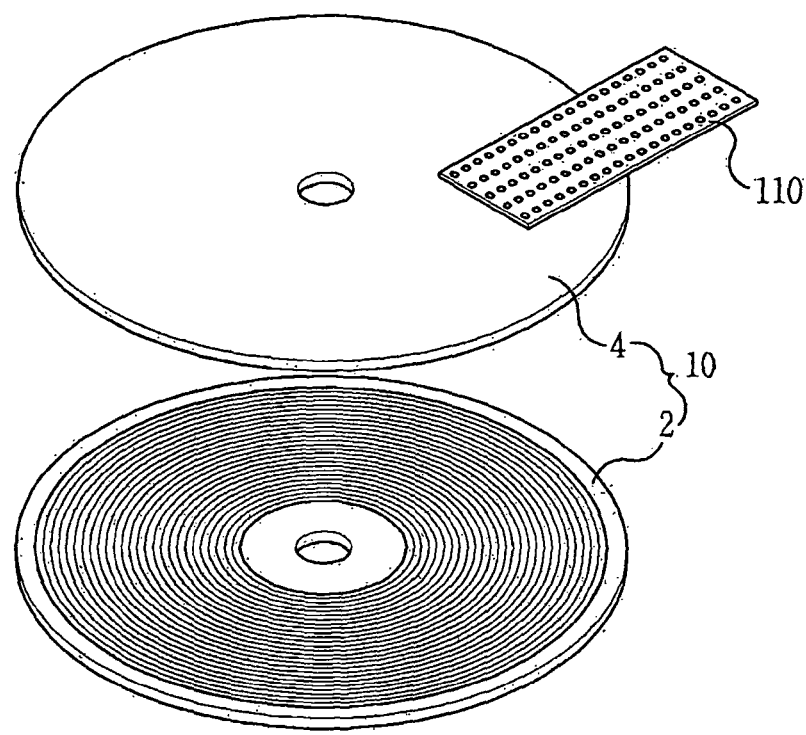
FIG. 8 is a view for describing a biochip cartridge.
Figure 9:
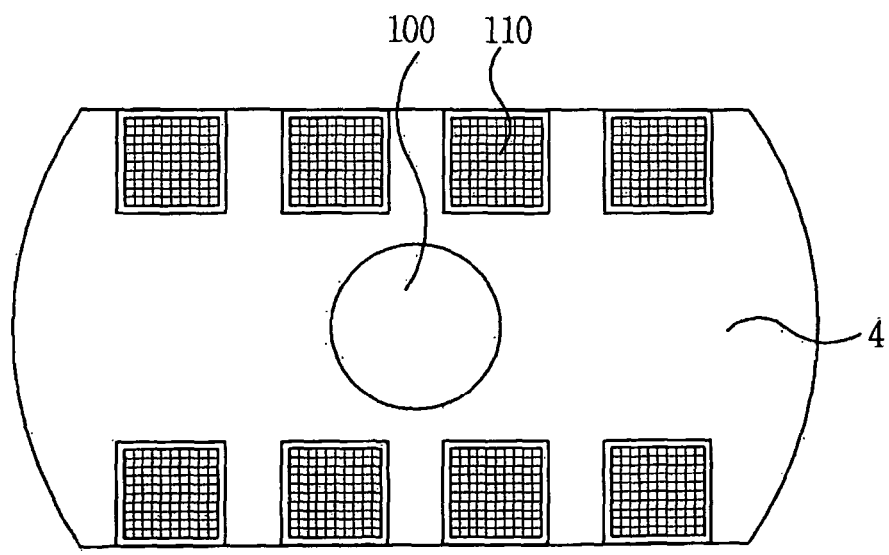
FIG. 9 is a view of a disc on which biochips are mounted.

Meanwhile, the above biochip 110 is used in a state of being mounted on the upper surface of the CD or DVD as mentioned above. Namely, as shown in FIG. 8, the biochip 110 is included on one side of the second substrate 4 located on the upper side of the first substrate 2 on which lands/grooves are formed, which is mounted on a general optical disc. Therefore, a sample can be read out as a beam scans bio-cells included in the biochip 110 using an optical disc reproduction/recording device. The bio-chip may be mounted on the optical disc using a variety of methods, which will be described in detail below.

Figure 10:
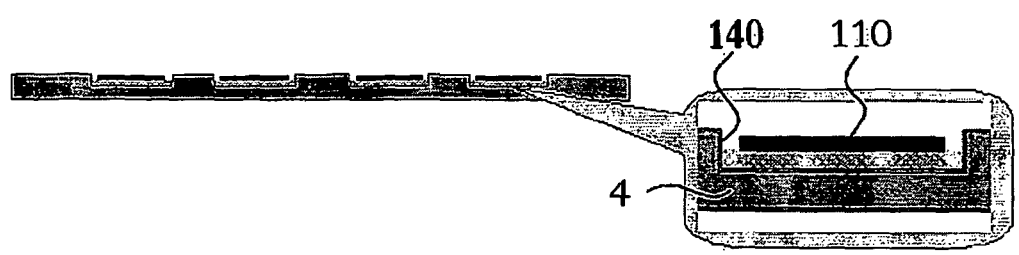
FIG. 10 is a view describing a state wherein the biochips of FIG. 9 are mounted on a disc.

As shown in FIG. 10, a groove 140 is formed on the upper side of the substrate 4 and then a biochip 110 is safely located therein. Here, the groove 140 has a depth such that the upper portion of the biochip 110 is lower than that of the substrate 4.

More specifically, as shown in FIG. 10, when the biochip is located in the groove 140, the biochip 110 is fixed to the bottom surface of the groove 140, which is coated with a binder, or by a fixing means (not shown) such that, even though the biochip mounting cartridge is rapidly rotated the biochip is not detached from the groove 140.

Figure 11:
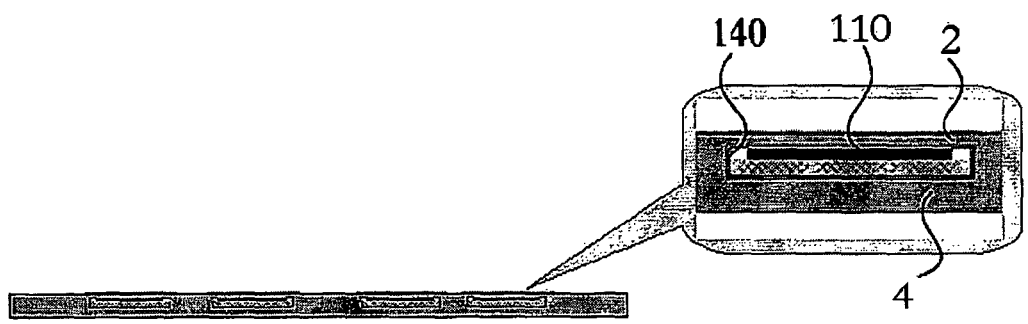
FIG. 11 is another embodiment of FIG. 10.

Meanwhile, instead of fixing the biochip 110 to the groove 140, it can be implemented like that the biochip 110 is located in the groove 140 formed on the upper side of the substrate 4 and then another substrate 5 is fixedly combined thereon such that the biochip 110 is placed between the substrate 4 and another substrate 5 as shown in FIG. 11.

When CD/DVD optical systems are used, the installation position of the biochip 110 installed on the groove 140 must match with that of the recording surface thereof. The methods of detecting a biochip installed in a groove are classified into a method of analyzing a biochip after the biochip is reacted in a sample solution and a method of analyzing a biochip just before the biochip is reacted in a sample solution. The former case is performed in the case that the biochip is placed between the substrates 4 and 2 as shown in FIG. 11 and the latter is performed in the case that the biochip is open at its upper surface as shown in FIG. 10.

As mentioned above, the biochip is reacted with the sample solution to reveal florescence of the result, which is detected by a method for detecting fluorescence revealing level using an optical disc record/reproduction device or a scanner.

As mentioned above, the optical disc can be used to mount a rectangular biochip. After detection, the installed biochip is separated from the optical disc to be replaced with a new biochip. When a user directly holds the rectangle-shaped biochip to install/separate it in/from the optical disc, errors or deformation may occur. Therefore, a holder shaped around the exterior shape, of the rectangle-shaped biochip is installed therewith such that the user can operate the biochip through the holder.

Also, in the optical disc with biochips mounted thereon a center hole is formed to couple with the rotation drive unit. The optical disc may have an inner diameter of 15 mm, a thickness of 1.2 mm and an outer diameter of 120 mm. Also, it may be a rectangular disc or it may be a combination disc combined a disc with a rectangular disc.

Meanwhile, the biochip 110 is formed on the upper side of the optical disc using a spotting method.

Figure 12:
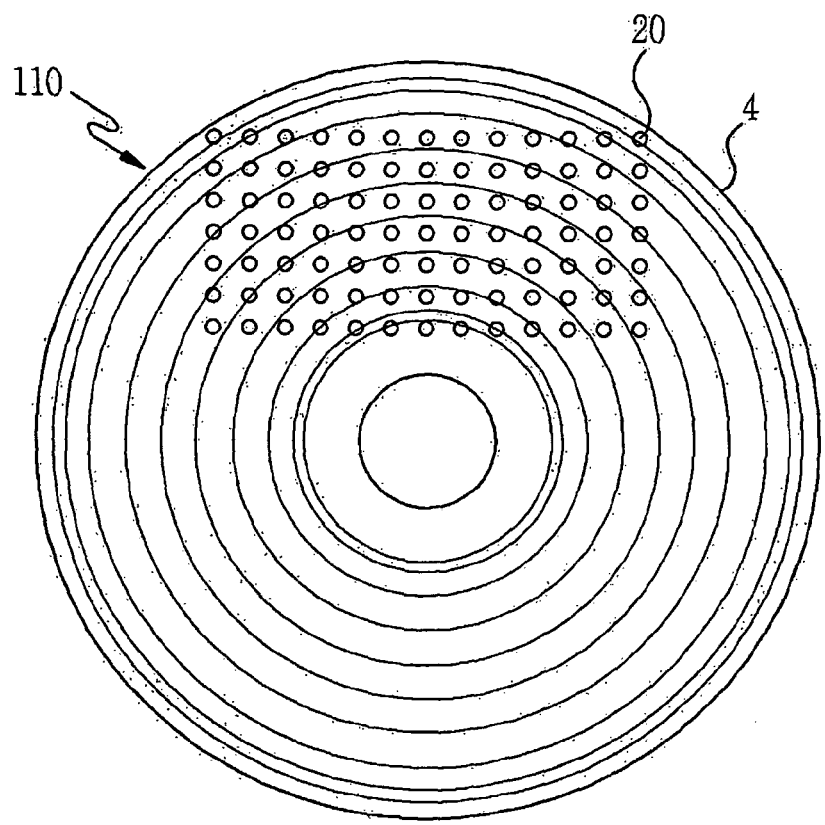
FIG. 12 is a view for describing a procedure for forming a biochip on a substrate in a spotting manner.
Figure 13:
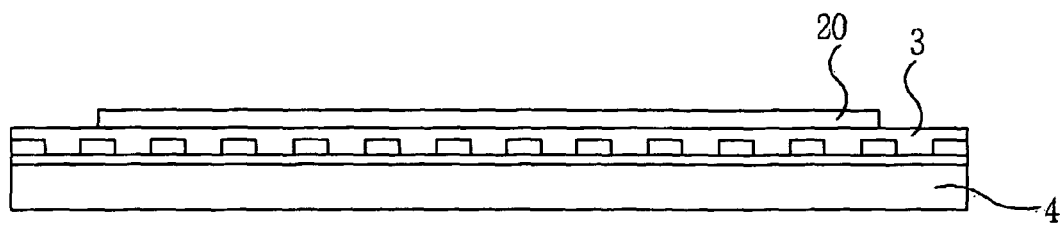
FIG. 13 is a cross-sectional view of FIG. 12.

Namely, as shown in FIGS. 12 and 13, the optical disc includes a substrate 4 on which lands/grooves are formed, a reflection substrate 3 reflecting a beam scanned from the optical pick-up to the upper side of the substrate 4, and biochip 110 including bio-cells 20 which are spotted on the upper side of the reflection substrate 3 in a predetermined pattern.

Here, the biochip spotting manner is achieved in the same fashion as the conventional manner. More specifically, the conventional biochips are spotted on a glass substrate, or a reflection film, in a predetermined interval arrange format using a linear stage manner. After a jig capable of being mounted on the disk thereon is manufactured, probes are spotted on the disc surface by the linear stage manner as in the prior art.

Figure 14:
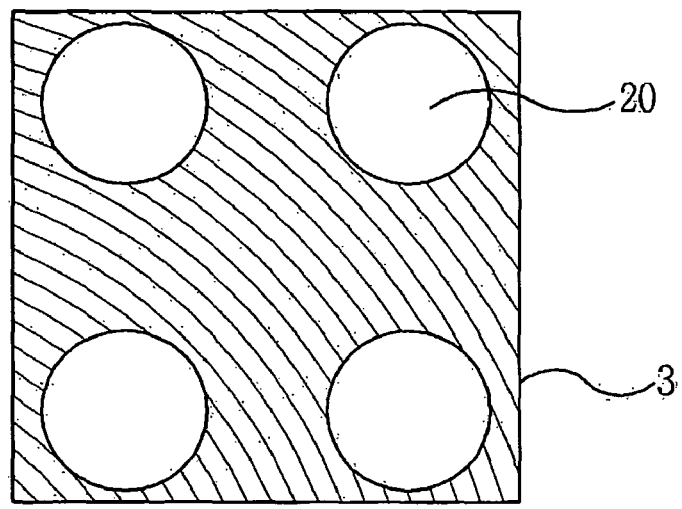
FIG. 14 is a view describing bio-cells included in a biochip.
Figure 15:
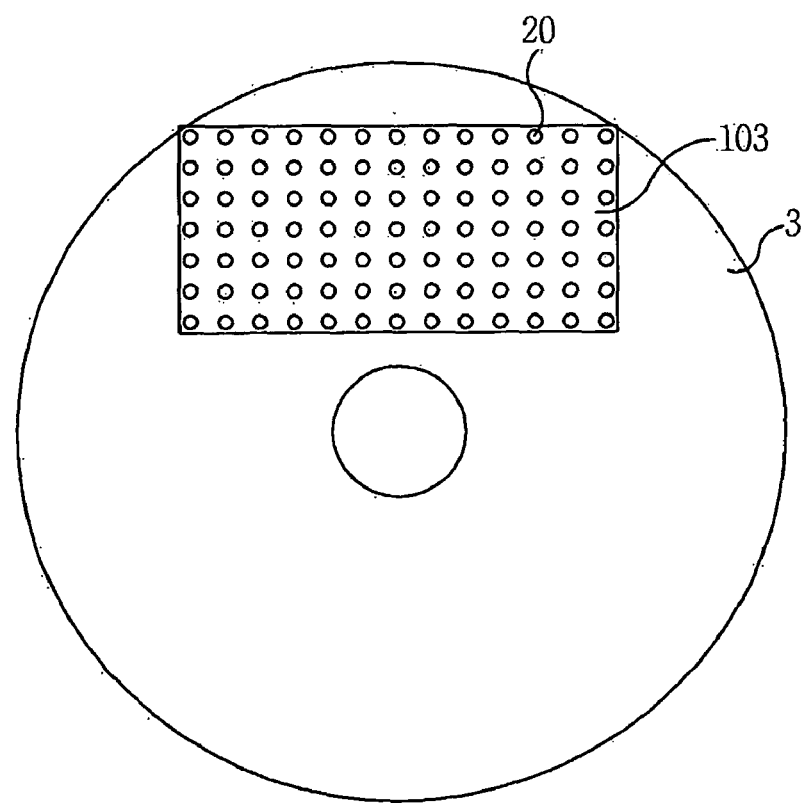
FIG. 15 is another embodiment of FIG. 12.
Figure 16:
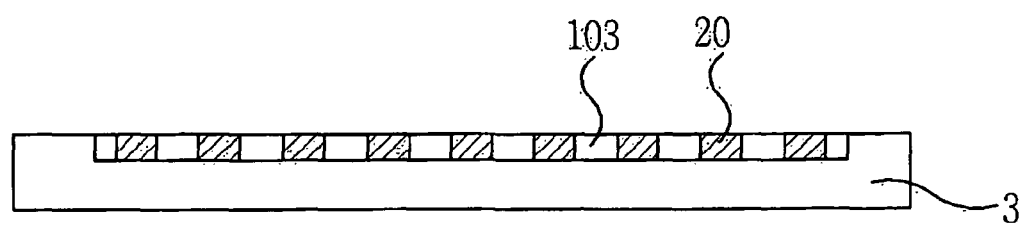
FIG. 16 is a cross-sectional view of FIG. 15.

Meanwhile, another spotting manner is described with reference to FIGS. 14 to 16. Grooves with a depth corresponding to a height (~a few μm) of bio-cell are on the upper side of the reflection substrate 3. The bio-cells form a bio-chip such that they are arranged in a rectangular format. The bio-cells 20 are formed in the groove in a spotting manner using a spotting device.

As such, as the bio-cells 20 are formed in the groove formed on the reflection substrate 3, they can be easily spotted thereon. Also, since the spotting method can remove height difference based on the bio-cells rather than the method for directly spotting bio-cells on the upper surface of the reflection substrate 3, signal for the focusing and tracking operations can be processed.

When information of a staring portion of a biochip is inserted into a reflection substrate 3, another portion and a portion including biochips can be separated with respect to a signal. Also, since bio-cells are located inside groove, they cannot be easily contaminated by dust or other substances, compared with the conventional biochip. Also, it has an advantage in that a scratch possibly generated in the surface can be prevented.

Also, as in the conventional disc structure, the lands/grooves formed in the disc are used for the focusing and tracking operations in an optical disc record/reproduction device for biochips.

Because each land/groove formed in the optical disc is a few hundred times smaller than the bio-cell, one bio-cell is divided into a plurality of pixels (about 100 by 100) and then scanned based on the division. Therefore, even though the bio-chip pattern has a structure not arranged in the periphery direction of the disc, information to a portion in which the bio-cells is scanned using a light emitting fluorescence detection head 22 having a relatively high performance. The scanned information is processed to generate images therefrom. Therefore, track pitch of the lands/grooves is a very important factor to accurately analyze biochips.

Also, a reflection film 3 formed on the optical disc is used for the focusing and tracking operations based on information reflected from a laser beam. Here, the thickness of the upper substrate formed on the reflection film 3 is a very important factor because it determines the spot size of the laser beam.

Figure 17:
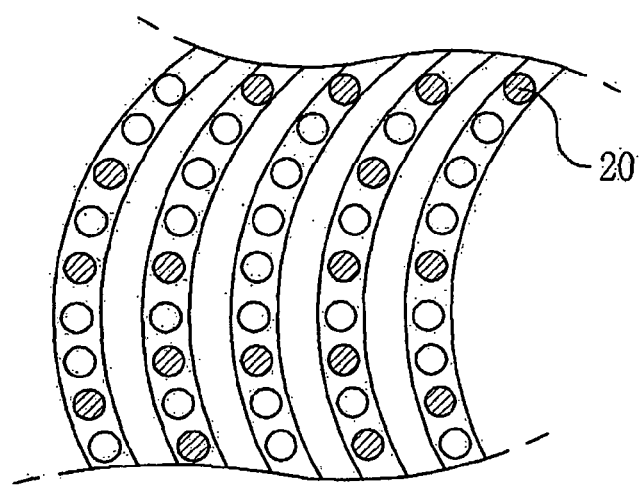
FIG. 17 is a view describing a procedure for forming bio-cells along with land/groove.

Here, in all the embodiments of the present invention, the substrate is made of a plastic such as polycarbonate. Even though polycarbonate has a lower flatness, but it has a high processibility. Because the substrate made of plastic can be mass-produced as it is processed by a method for forming lands/grooves fitting to bio-cell size, as shown in FIG. 17, such that an optical pick-up adopting a general optical disc manner can perform tracking operation low manufacturing costs are relatively low. Therefore, the disc with biochips mounted thereon can also be provided at a relatively low price.

In the conventional art, since the bio-cells are directly spotted on the glass substrate, the forms of the bio-cell grids are non-uniform and boundaries therebetween are not distinct such that errors occur when bio-cells are detected. Therefore, the conventional art further requires a statistical method such as infomatix to process the errors. In the case that the substrate made of a plastic for biochips, in which plastic has a good forming ability, is used, patterned grids can be easily formed on the disc along the periphery thereof by a biochip patterning apparatus which will be described later and can be clearly the boundaries based on a spotting manner. The bio-cell can be more clearly formed compared with the conventional manner. Therefore the method of the present invention can perform a highly accurate detection operation, compared with the conventional method.

Figure 18:
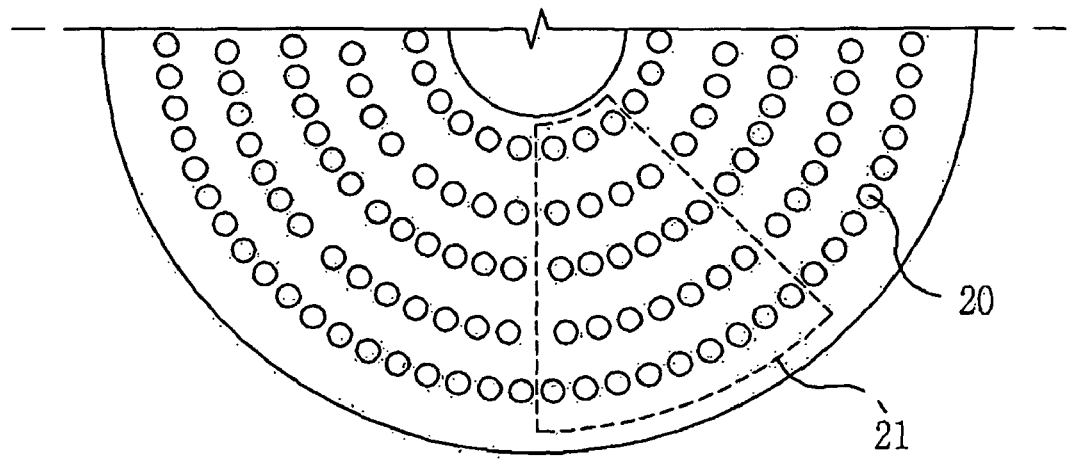
FIG. 18 is a view describing a procedure for forming bio-cells on land/groove by classifying predetermined area when the bio-cells are formed in the manner of FIG. 17.

Also, as shown in FIG. 18, when bio-cells are spotted on the disc by a rotation manner based on a plurality of areas displayed by dotted-lines, the plurality of areas can be detected, respectively and have information, respectively. Namely, if the disc pattern divides the disc into a predetermined number of areas such that each area corresponds to a biochip, a plurality of biochips are simultaneously detected.

In order that biochips are read out from a DVD, for example, bio-cells are attached on the upper surface of the transparent plastic substrate, which is 0.6 mm thick, or biochips are installed on the upper surface of a disc adapter manufactured as a substrate having a thickness of 0.6. Discs manufactured by the above method are not easily affected by dust or other foreign matter and have an advantage in that focusing and detection can be performed simultaneously. Here, the thickness of the substrate may be varied according to a detection design.

Figure 19:
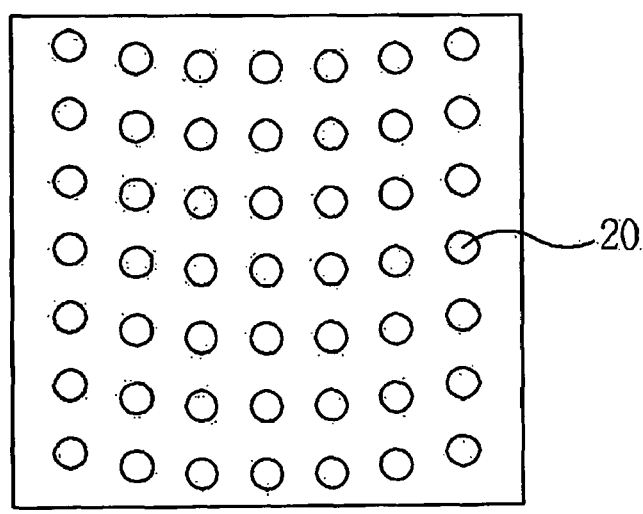
FIG. 19 is a view illustrating bio-cells formed in a disc.

When bio-cells are formed in a disc using pin module as a biochip patterning apparatus, which will be described later, the bio-cells are effectively formed on a biochip installed in a disc or a disc-shaped cartridge, as shown in FIG. 19.

Bio-cell Patterning Device for Biochip

As shown in FIGS. 20 to 23, a bio-cell patterning device for forming a biochip on a disc may be applied to various embodiments, each of which is described in detail below.

Figure 20:
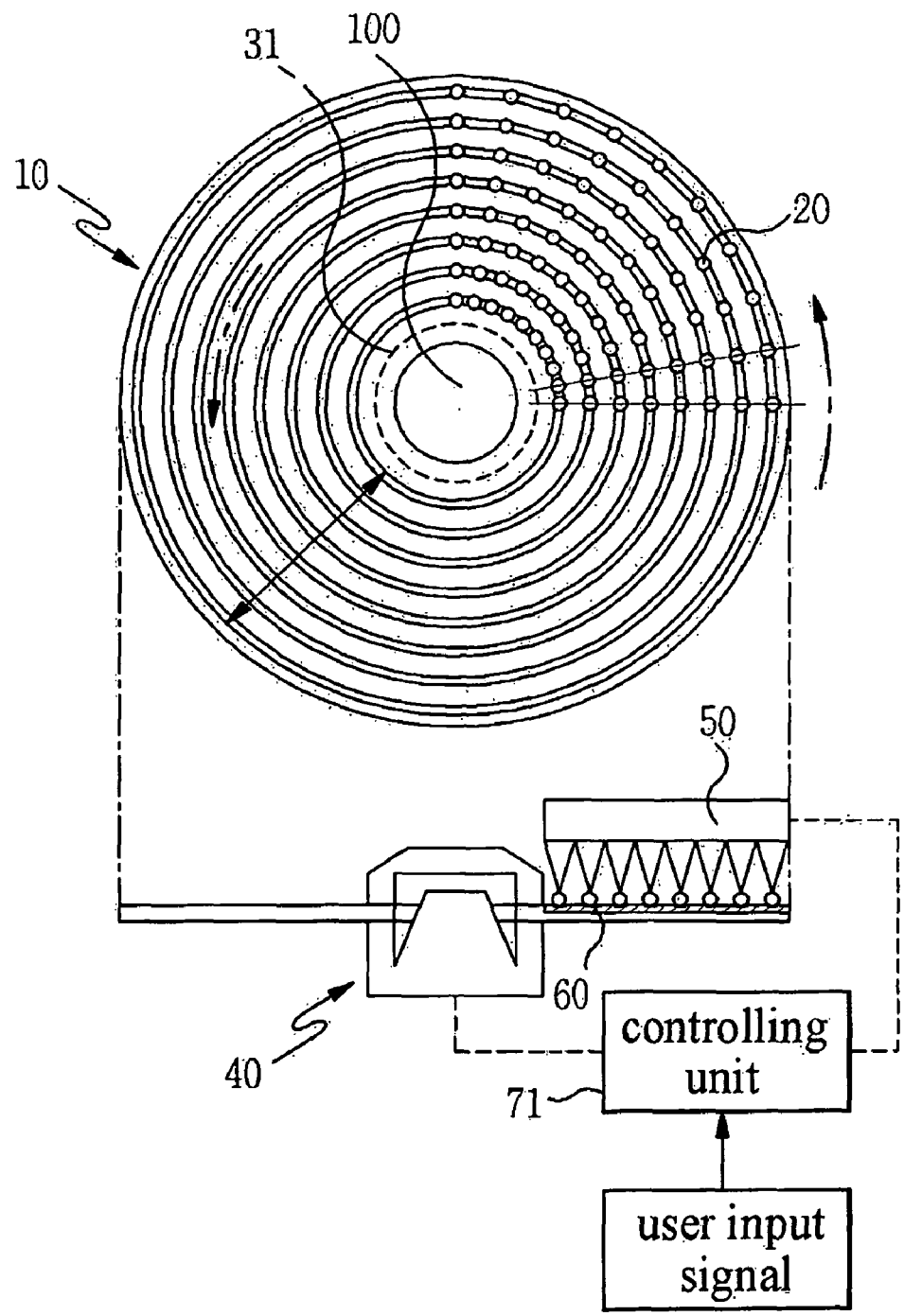
FIG. 20 is a view for describing an apparatus for patterning bio-cells.

More specifically, as shown in FIG. 20, the bio-cell patterning device forms a biochip on an optical disc 10, in which the optical disc 10 includes a center hole 100 at the center thereof, an area 31 for storing bio-cell position information at a predetermined radius with respect to the center hole and a bio-cell pattern area forming bio-cell patterns at outer area of the bio-cell position information storing area 31. The bio-cel patterning device includes a servo device 40 coupling with the center hole 100 of the optical disc 10 such that the optical disc 10 can rotate at predetermined rotation speed, a printer for patterning bio-cells on the bio-cell patterning area, in which the printer includes a pin module 50, and a controlling unit 71 for driving the servo device 40 to rotate the optical disc 10 according to a user control and controlling the entire system such that bio-cell patterns are printed on the upper surface of the optical disc through the pin module 50 of the printer.

The pin module 50 of the printer is implemented with a type of a single pin module capable of entirely patterning bio-cells on the bio cell pattern area of the optical disc while the optical disc 10 rotates at one turn.

The cell position information storing area 31 stores initial information or position information of each spot, or information for tracks and bio-cells, when detecting biochips based on rotation of the optical disc.

Operations of the bio-cell patterning device as constructed above are described in detail below.

Firstly, the optical disc 10 is mounted on the servo device 40 such that the center hole 100 of the optical disc 10 is fitted on the chuck of the servo device 40. When a predetermined input signal, i.e., a bio cell pattern generation signal, is inputted to the controlling unit 71, the controlling unit 71 controls the servo device 40 in response to the bio cell pattern generation signal such that a spindle motor of the servo device 40 can rotate at a constant speed.

After that, the controlling unit 71 controls the pin module 50 to form a bio cell pattern on the upper surface of the optical disc. Namely, the pin module 50 is arranged to cover one side of the bio cell pattern area from the center hole to the outer periphery in the radial direction. Therefore, while the optical disc rotates one turn according to the servo device 40, the pin module 50 is repeatedly operated for a predetermined time period such that bio-cells are scanned on the upper surface of the optical disc to form a biochip thereon.

Figure 21:
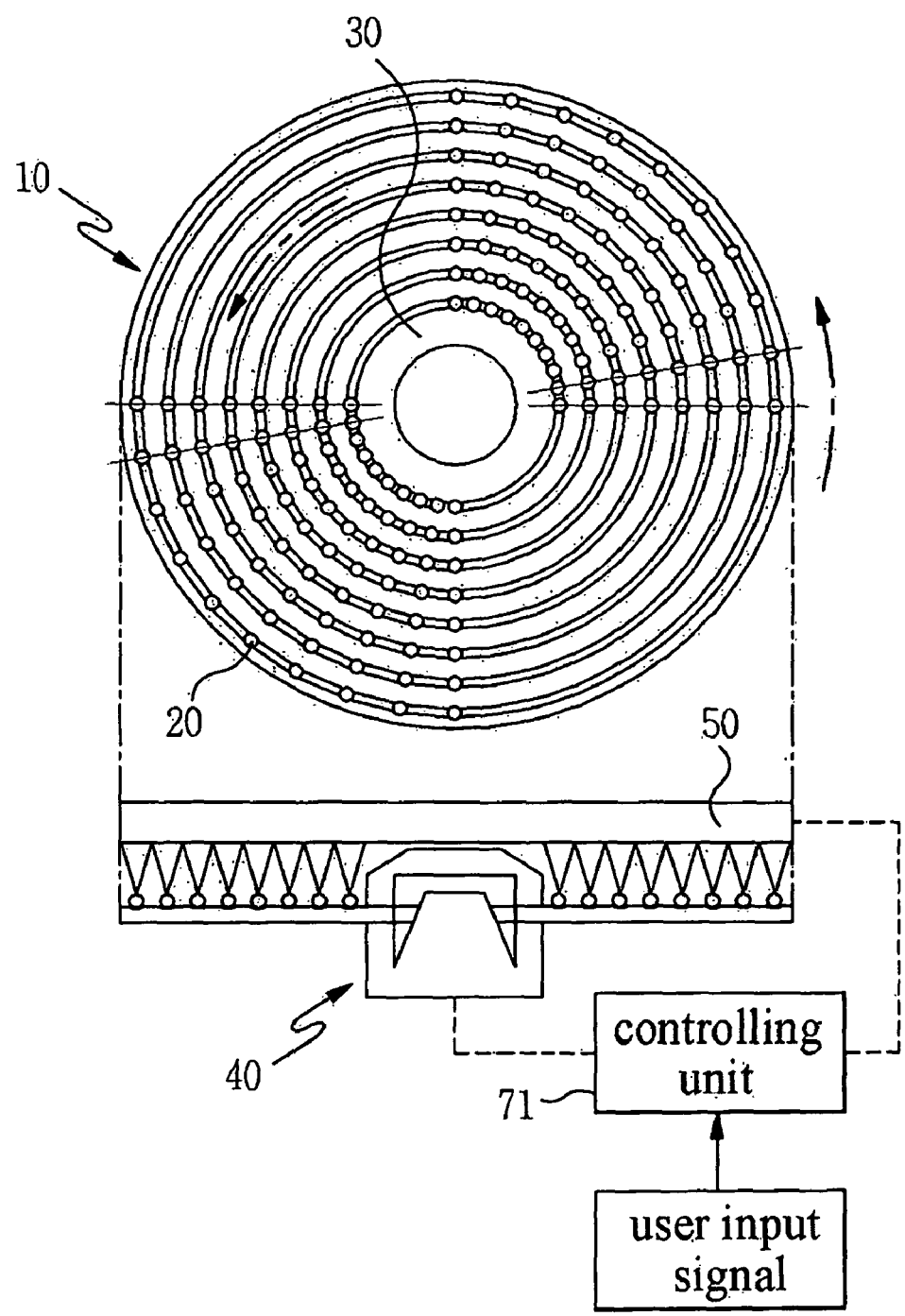
FIG. 21 is a view of a second embodiment of FIG. 20.
Figure 22:
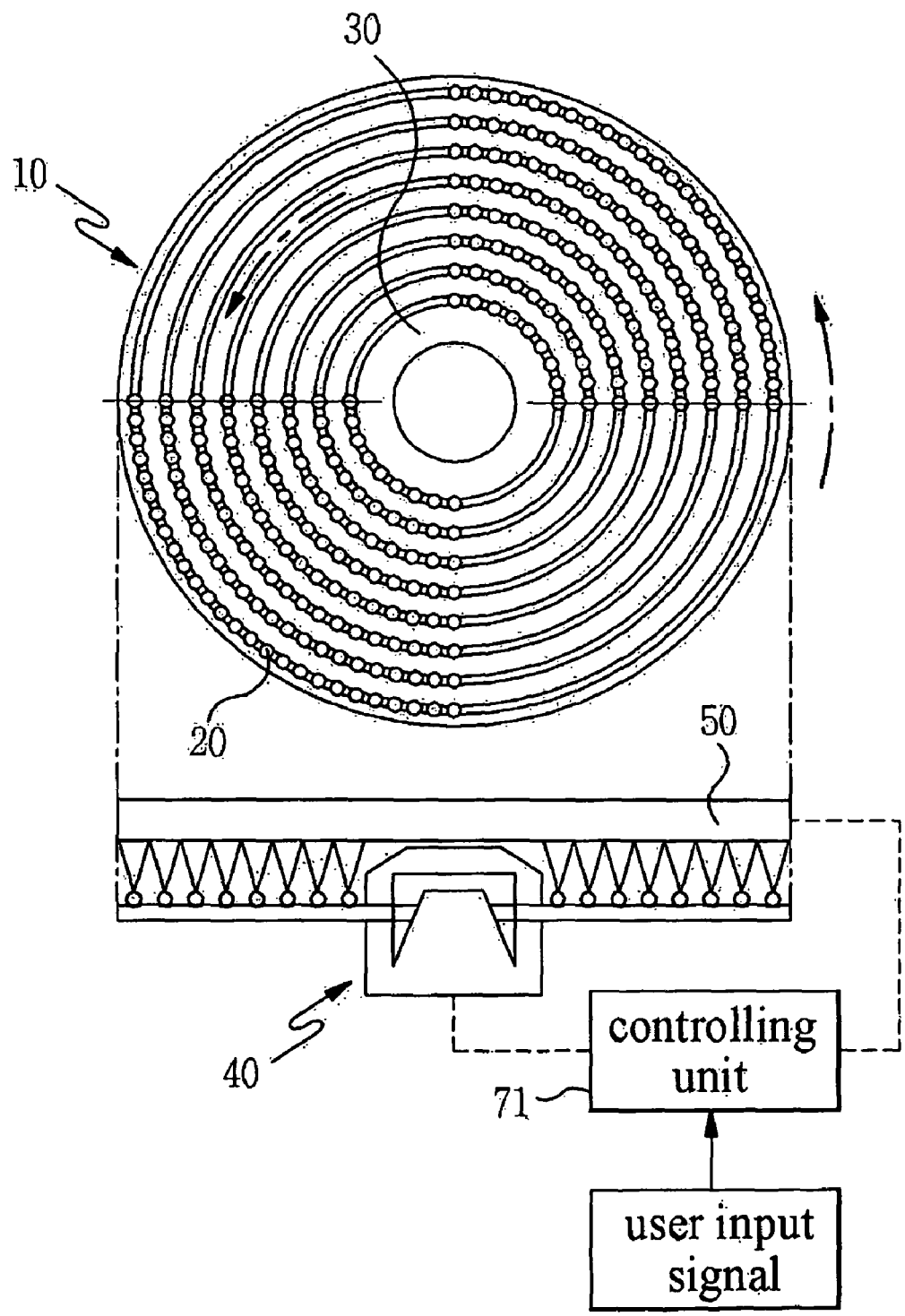
FIG. 22 is a view of a modification embodiment of FIG. 21.

Meanwhile, the bio-cell patterning device of FIG. 21 has a structure similar to that of the bio-cell patterning device of FIG. 22 except for a pin module 50. Here, only the pin module 50 of the bio-cell patterning device of FIG. 21 is described in detail below.

As shown in FIG. 21, the pin module 50 is arranged to cover both sides of the bio cell pattern area from the center hole to the outer periphery in the radial direction. Therefore, while the optical disc rotates a half turn, the pin module 50 is repeatedly operated for a predetermined time period such that bio-cells are scanned on the bio cell pattern area to form bio cell pattern thereon. Here, the controlling unit 71 controls the entire system such that the bio-cells 20 are scanned on the upper surface of the optical disc to form a cell pattern according to a concentric-circle type constant angular velocity (CAV) manner. Accordingly, the bio-cells are formed in the optical disc 10 such that the more the bio-cells are relatively densely located to each other in relatively inner circles the less the bio-cells are relatively farther located to each other in relatively outer circles.

When the bio cell pattern is formed on an optical disc according to the concentric-circle type constant angular velocity (CAV) manner, a mechanism for patterning bio-cells on the optical disc can be easily implemented. Therefore, the bio-cell pattern can be detected at a constant angular velocity of the optical disc.

Even if it is not shown in the drawings, the controlling unit 71 may control the servo device 40 to pattern bio-cells on the optical disc based on a zone CAV manner modified from the concentric-circle type CAV manner. Namely, the controlling unit 71 controls the servo device 40 such that the rotation speed of the optical disc is reduced step wise based on a predetermined area in the bio cell pattern area to achieve a predetermined constant velocity in the predetermined area while the pin module is moved from the inner radius of the optical disc to the outer radius, in which the radius difference corresponds to the predetermined area. More specifically, when the pin module is in a first predetermined area, the bio cells are patterned therein at a predetermined constant angular velocity while the optical disc is rotated at a first rotation speed. After that, the controlling unit 71 controls the servo device 40 such that the rotation speed of the optical disc is reduced less than that in the first predetermined area to achieve a predetermined constant velocity therein when the pin module is moved to a next area by a predetermined distance from the first area. Then the bio-cells are patterned in that area. These processes are continued to the most outer periphery. Therefore the zone CAV manner can pattern bio-cells in the bio cell pattern area more densely than the concentric circle type CAV manner.

As shown in FIG. 22, the bio-cell patterning device is operated such that a controlling unit 71 controls a servo device 40 to maintain its constant patterning speed. Namely, the servo device is rotated in a constant linear velocity (CLV)

manner to form a predetermined bio-cell pattern on the upper surface of the optical disc, in which bio-cells are spaced apart from each other with the same interval at every track. Because the bid-cells 20 are formed with a constant interval on inner radius and outer radius of the optical disc 10, the optical disc can maximumly store as much information as its physical area allows. Therefore, the bio-cell patterning device of FIG. 22 enables the biochip to have a high density rate.

Figure 23:
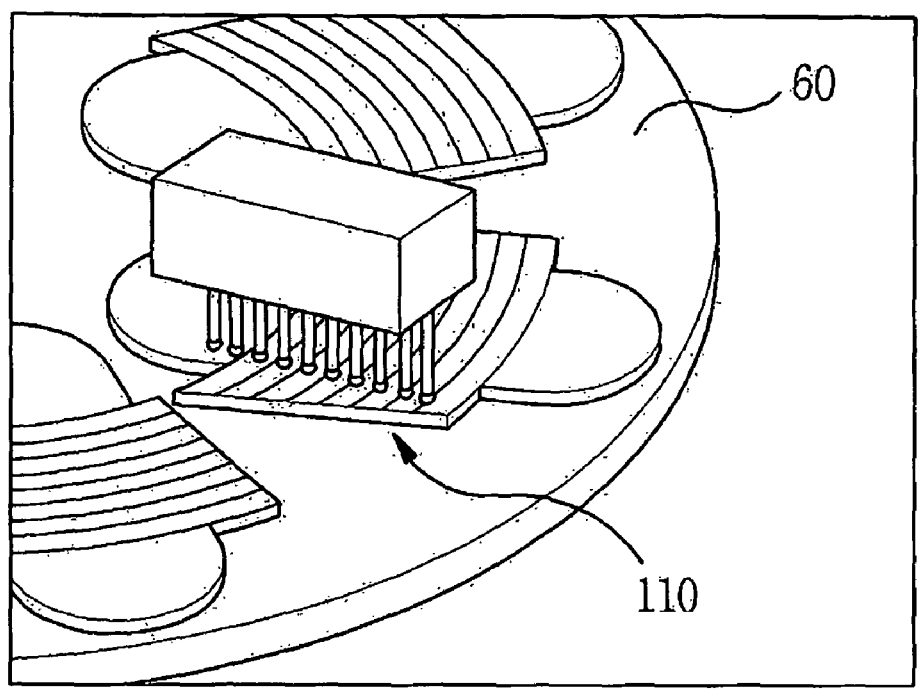
FIG. 23 is a view of a third embodiment of FIG. 20.

As shown in FIG. 23, bio-chips 110 are installed on the upper surface of the optical disc 10. A controlling unit (not shown) controls a pin module 50 and a servo device 40 such that bio cells 20 are patterned on each of the biochips 110 through the pin module 50. Namely, a conventional rectangular biochip is patterned by a cartridge for a disc type biochip installation, in which the biochip is attached to the disc by an adhesive means or by a disc type biochip which are divided into a plurality of areas. Here, since the manner for patterning bio cells in the biochip 110 is similar to that of the previous embodiments, a description of the operations thereof will be omitted.

Here, the adhesive means has a sufficient adhesive strength to prevent the biochip from moving during rotation of a cartridge for biochip installation.

Meanwhile, the method for fixing biochips to a cartridge for biochip installation may be implemented with various manners including a method using an adhesive as mentioned above, such as a method using a fixing means for generating grooves and fixing biochips to the generated grooves.

Diagnostic System

A diagnostic system can be constructed using the biochip readout device 100 according to the present invention and is described in detail with reference to FIG. 24.

Figure 24:
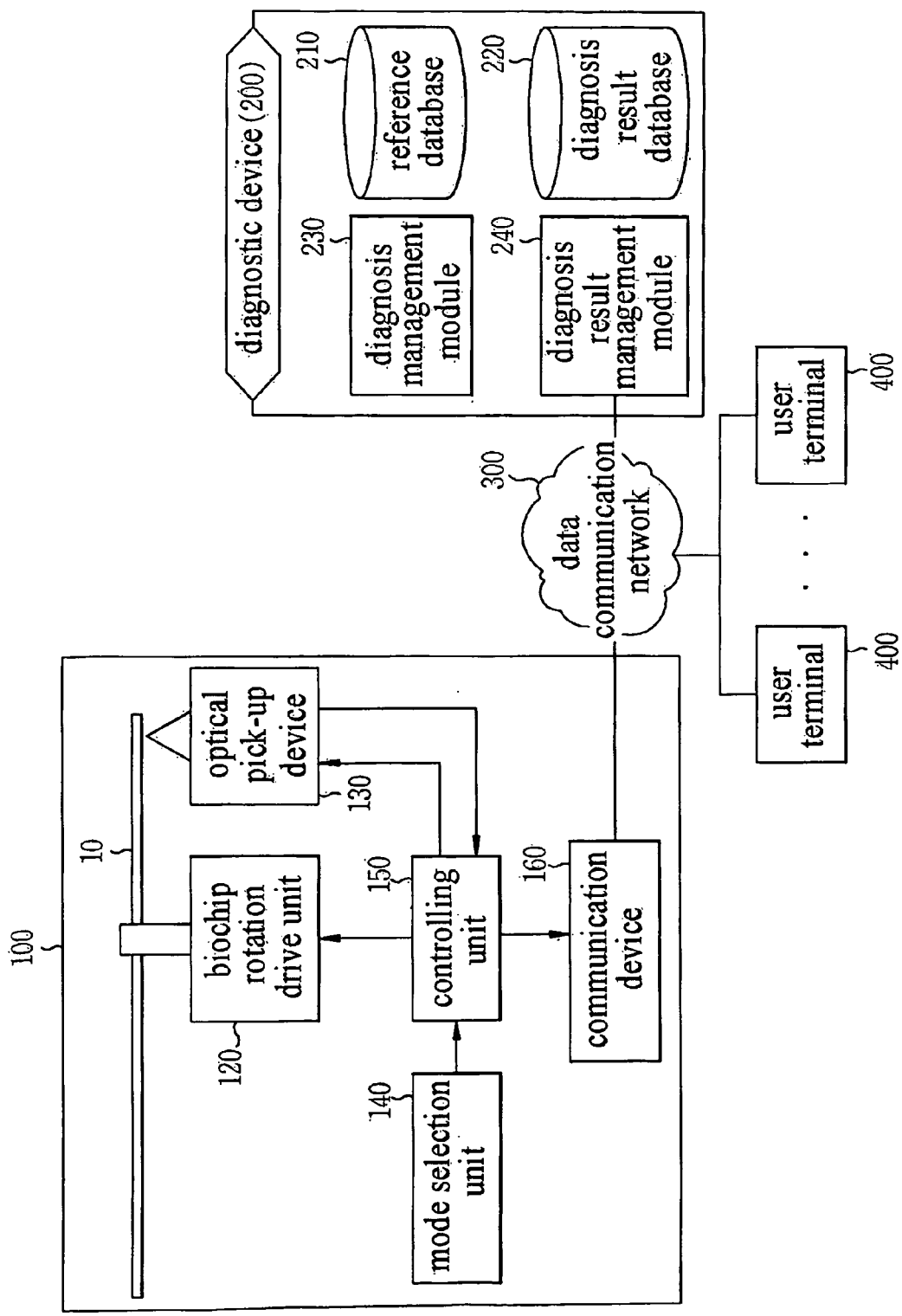
FIG. 24 is a view illustrating the construction of the diagnostic system according to the present invention.
Figure 25:
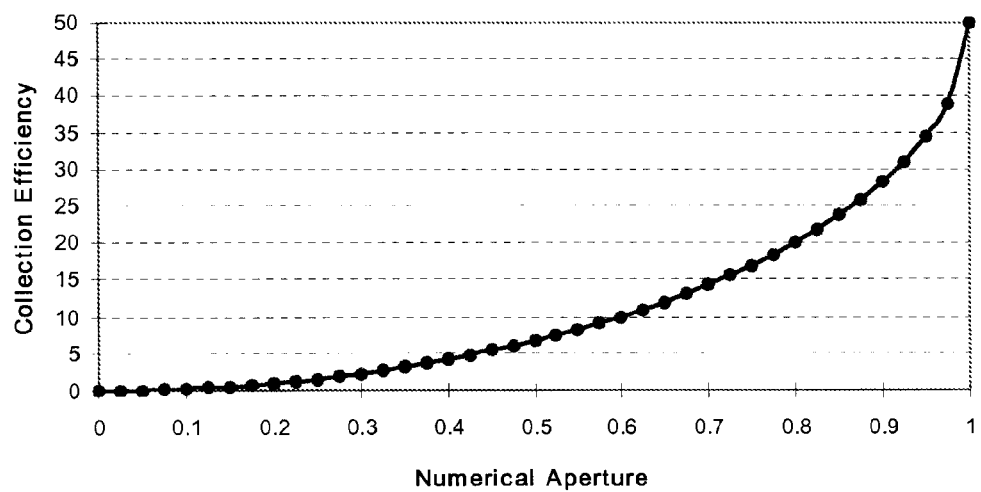
FIG. 25 is a graph showing collection efficiency as a function of numerical aperture for a prior-art optical collector.

As shown in FIG. 24, the diagnostic system includes a biochip readout device 100, a diagnosis apparatus 200 as a server, and a data communication network 300 connecting the biochip readout device 100 with the diagnosis apparatus 200.

Here, since the biochip readout device 100 is similar to the previous embodiment of the present invention, a detailed description is omitted below.

The diagnosis apparatus 200 includes a reference database 210 for storing reference data to monitor biomaterial of biochips, a diagnosis result database 220, a diagnosis management module 230 for comparing biomaterial analysis request data from the biochip readout device 100 with reference data from the reference database 210, analyzing the result of the comparison, registering and storing the analysis result or the analyzing operation to the diagnosis result database 220 and providing the analysis result to a user, and a diagnosis result management module 240 for sending a diagnosis result corresponding to the analysis result registered in the diagnosis result database 220 to a user terminal 400 in response to transmission information from a communication device 160 of the biochip readout device 100 based on a request of the diagnosis management module 230. Here, the analyzing result is used for monitoring the biomaterial of the biochip.

Here, the reference data registered in the reference database 210 is statistical data generated by doctors or experts, which is used to compute probability of diseases, incidence rate, prevalence rate and an attack rate.

Operations of the diagnostic system as constructed above are described in detail below.

Because the operations of the biochip readout device 100 are similar to the previous embodiment of the present invention, a detailed description therefor is omitted below.

The biomaterial analysis request data generated in the biochip readout device 100 is transmitted to the system and output controlling unit 150 and the communication device 160. The biomaterial analysis request data transmitted to the communication device 160 is inputted to the diagnosis management module 230 of the diagnosis apparatus 200 via the data communication network 300.

The diagnosis management module 230 compares the biomaterial analysis request data with the reference data registered in the reference database 210, determines a particular disease or a presence of an symptom based on the comparison, provides them to a user, and computes a probability of diseases, incidence rate, prevalence rate and an attack rate.

Here, the biochip analysis system 100 transmits biochip-specific information and the biomaterial analysis request data together in response to a user request thereto. The diagnosis management module 230 registers the received biochip-specific information and the biomaterial analysis request data to the diagnosis result database 220, associating with each other, and manages them. Also, the diagnosis management module 230 transmits the diagnosis result to a user terminal 400 under control of the diagnosis result management module 240.

INDUSTRIAL APPLICABILITY

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

The invention claimed is:

1. A diagnostic system having a biochip readout apparatus, comprising:
 a biochip readout device including: a biochip cartridge comprising: (i) an optical disc comprising a first and a second substrate and a selective wavelength reflection film disposed on the first substrate, the first substrate having one or more substantially circular lands and grooves formed thereon, the second substrate having one or more depressed portions formed therein; and (ii) at least one or more preformed biochips each comprising bio-cells spotted on the second substrate and forming an array having a substantially square or rectangular shape; wherein the at least one or more biochips are removably installed in each of the depressed portions such that the at least one or more biochips cannot be separated from the optical disc when the optical disc is rotated or moved or the biochip is combined with another substrate thereon; and the selective wavelength reflection film is disposed between the one or more biochips and the first substrate;
 a disc rotation drive unit driven such that the biochip cartridge is rotated;
 a system and output controlling unit for outputting monitoring bio analysis information, the system and output controlling unit having a signal processing unit for processing and analyzing the bio analysis signal corresponding to bio analysis information to generate the monitoring analysis information;
 an optical pick-up device comprising:
 a light receiving unit comprising one or more light sources and one or more light detectors wherein the one or more light detectors is a photomultiplier tube or photodiode; wherein light from the one or more light sources is reflected by the reflective coating of the selective wavelength reflection film of the biochip cartridge and is detected by the one or more light detectors to obtain tracking and focusing signals for the optical pick-up device; and light from the one or more light sources causes the one or more biochips to emit a fluorescent signal that is detected by the one or more light detectors;

a focusing/tracking controlling unit for controlling a focusing and tracking operation of the optical pick-up device using the tracking and focusing signals from the first light detector, so that the light from the one or more light sources tracks along the one or more lands and grooves of the biochip cartridge;

an objective lens driving unit for focusing the light from the one or more light sources;

a bio analysis signal generation unit for receiving the fluorescent signal emitted by the one or more biochips and outputting a bio analysis signal; and an optical recording/reproducing unit for recording a recording bio analysis signal in a predetermined area of the biochip cartridge in response to a control signal of the system and output controlling unit and reproducing recorded bio analysis information;

a mode selection unit for selecting one of a biochip readout mode and a general optical recording/reproducing mode; and a diagnosis device for comparing the monitoring bio information for monitoring image signal from the biochip readout device with reference data and proving an analysis result generated based on a result of the comparing operation to a user, wherein the reference data for monitoring bio-information of the biochip are constructed in database format in the diagnosis device.

2. The biochip readout device as set forth in claim 1, wherein the bio analysis signal generation unit of the optical pick-up device scans the biochip cartridge with light in response to a control signal inputted from the system and output controlling unit, in case that the optical pick-up device has a single light source, and, at the same time, outputs a focusing/tracking controlling signal and the bio analysis signal caused by the light excited by the biochip.

3. The biochip readout device as set forth in claim 2, wherein the system and output controlling unit forms a matrix structure such that a cell revealing florescent dye is recognized as a letter of A and other cells are recognized as a letter of ~A, and generates monitoring bio analysis information based on the matrix structure.

4. The biochip readout device as set forth in claim 3,
wherein the bio analysis signal generation unit comprises:
an excited florescence filter for filtering an excited florescence wave of lights excited by the biochip; and
an excited florescent wave head for outputting the bio analysis signal based on detection of the filtered excited florescence wave in response to the control signal inputted from the system and output controlling unit.

5. The biochip readout system as set forth in claim 1, further comprising a communication device for transmitting an analysis processing request data together with the monitoring image signal thereto after inputting the monitoring image signal to analyze bio-matter from the biochip readout device and connecting communication lines thereto based on predetermined communication connection information.

* * * * *